United States Patent [19]

Razdolsky et al.

[11] Patent Number: 5,599,183

[45] Date of Patent: Feb. 4, 1997

[54] ASSEMBLY TOOL FOR ASSEMBLING A MANDIBULAR DISTRACTION DEVICE

[76] Inventors: Yan Razdolsky, 600 Lake Cook Rd., Suite 150, Buffalo Grove, Ill. 60089; Patrick J. Driscoll, 203 E. Olive, Prospect Heights, Ill. 60070

[21] Appl. No.: 222,579

[22] Filed: Apr. 4, 1994

[51] Int. Cl.[6] .................................................. A61C 3/00
[52] U.S. Cl. ............................... 433/53; 433/60; 269/45
[58] Field of Search ................................ 433/49, 53, 54, 433/60, 61, 62, 63, 64, 65, 24, 25; 269/37, 45, 46, 56, 58, 60, 76, 254 R, 254 DF, 309; 248/125.1, 288.51, 298.1, 316.5

[56] References Cited

U.S. PATENT DOCUMENTS

| | | | |
|---|---|---|---|
| 1,005,010 | 10/1911 | Farnsworth | 269/45 |
| 1,096,195 | 5/1914 | Roberts | 433/60 |
| 2,221,108 | 11/1940 | Rathbun | 269/45 |
| 2,322,380 | 6/1943 | Mosley, Jr. | 269/76 |
| 2,773,303 | 12/1956 | Tirone | 369/76 |
| 3,277,576 | 10/1966 | Kraft | 433/53 |
| 3,385,540 | 9/1974 | Biederman . | |
| 4,070,011 | 1/1978 | Glesser | 269/45 |
| 4,174,570 | 11/1979 | Schwartz | 433/53 |
| 4,358,269 | 11/1982 | Hay et al. | 433/60 |
| 4,370,129 | 1/1983 | Huge . | |
| 4,482,318 | 11/1984 | Forster . | |
| 4,507,084 | 3/1985 | Blechman et al. . | |
| 4,571,177 | 2/1986 | Dahan . | |
| 4,571,178 | 2/1986 | Rosenberg . | |
| 4,573,914 | 3/1986 | Nord . | |
| 4,723,910 | 2/1988 | Keller . | |
| 4,741,696 | 5/1988 | Cetlin . | |
| 4,802,849 | 2/1989 | Collins, Jr. . | |
| 5,002,485 | 3/1991 | Aagesen . | |
| 5,007,828 | 4/1991 | Rosenberg . | |
| 5,133,659 | 7/1992 | Shilliday . | |
| 5,167,499 | 12/1992 | Arndt et al. . | |
| 5,167,500 | 12/1992 | Miura . | |

OTHER PUBLICATIONS

Professor Gavriel A. Ilizarov, M.D., The Principals of the Ilizarov Method, Bulletin of the Hospital for Joint Diseases Orthopaedic Institute, vol. 48, No. 1, 1988 pp. 1–11.

Nolan S. Karp, M.D., Charles H. M. Thorne, M.D., Joseph G. McCarthy, M.D., Hubert A. Sissons, M.D., Bone Lengthening in the Craniofacial Skeleton, Annals of Plastic Surgery, vol. 24, No. 3, Mar. 1990, pp. 22–28.

Cliffored C. Snyder, M.D., George A. Levine, M.D., Howard M. Swanson, D.D.S., Earl Z. Browne, Jr., M.D., Mandibular Lengthening by Gradual Distraction (Preliminary Report), Plastic and Reconstructive Surgery, vol. 51, No. 5, pp. 506–508.

Peter D. Costantino, M.D., George Shybut, M.D., Craig D. Friedman, M.D., Harold J. Pelzer, D.D.S., M.D., Michael Masini, M.D., Maisa L. Shindo, M.D., Craig A. Sisson, Sr., M.D., Segmental Mandibular Regeneration by Distraction Osteogenesis, Arch Otolaryngol Head Neck Surg, vol. 116, May 1990, pp. 535–545.

Michael S. Block, D.M.D., John Daire, D.D.S., John Stove, D.D.S., Murray Matthews, P.h.D., Changes in the Inferior Alveolar Nerve Following Mandibular Lengthening in the Dog Using Distraction Osteogenesis, American Association of Oral and Maxillofacial Surgeons, pp. 652–660.

Pro Lab Services, Functionals, Brochure with Handwritten Page Nos. 3–9.

Primary Examiner—David A. Wiecking
Attorney, Agent, or Firm—Wenderoth, Lind & Ponack

[57] ABSTRACT

Mandibular distraction osteogenesis can take place by performing corticotomy surgery at two points on opposite sides of the mandible and at the same time attaching an expansible distraction device to the teeth of the mandible on opposite sides of the two points of the corticotomy surgery. The device is then periodically expanded until a desired mandibular length is obtained. The device includes a plurality of bands that are fitted onto the teeth of the mandible and a number of universal expansion screws that are connected to the bands for purposes of distracting the mandible. This device can be assembled with an appropriate appliance assembly tool that precisely positions and aligns the universal expansion screws relative to the bands during assembly thereof.

22 Claims, 12 Drawing Sheets

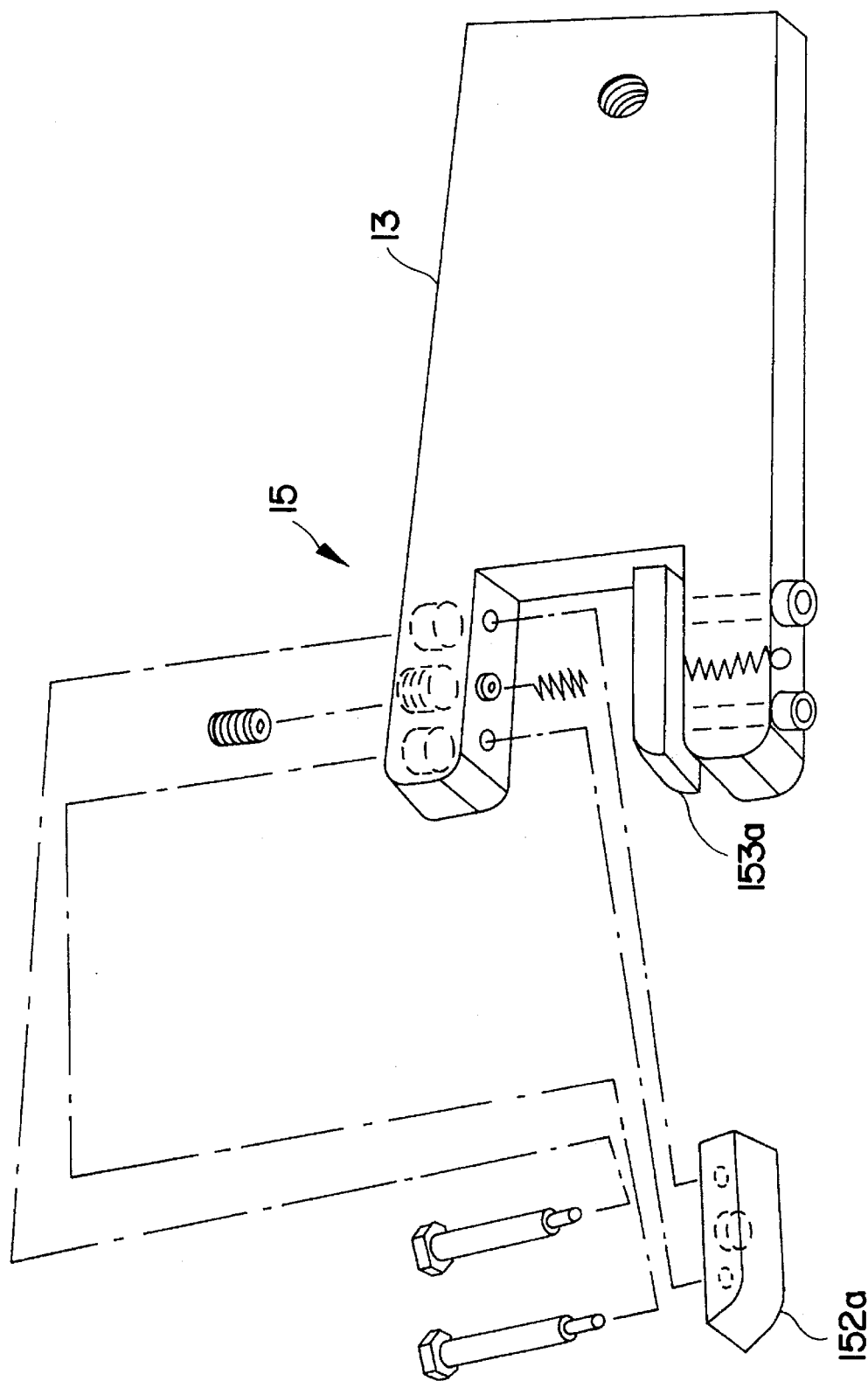

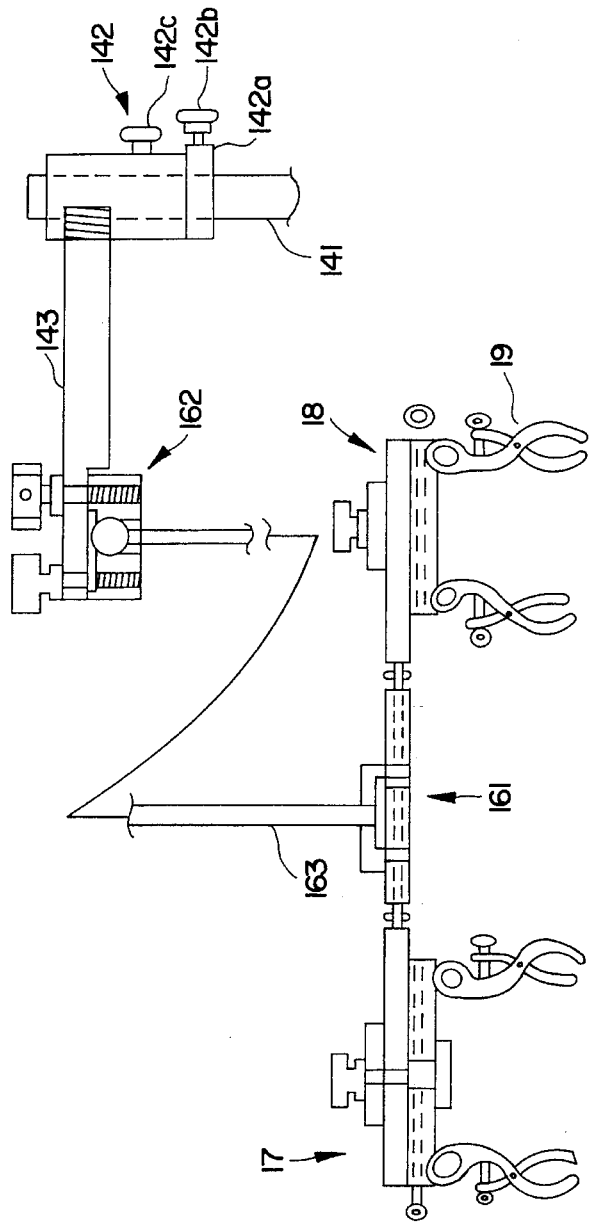
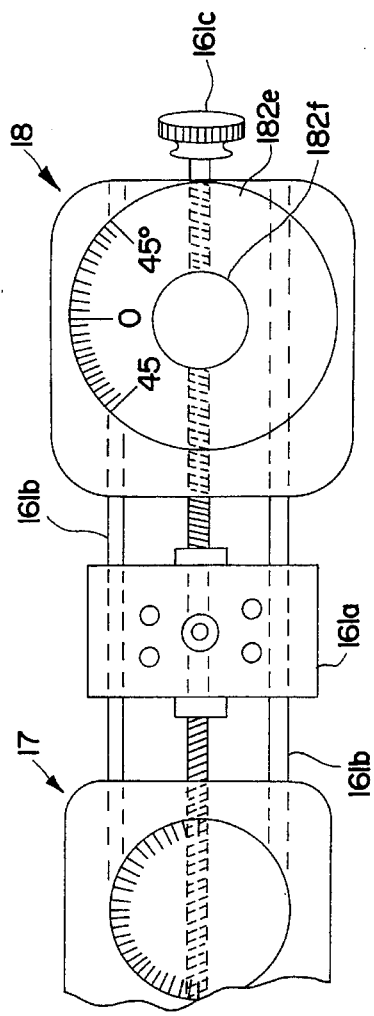
FIG. 7
FIG. 8A

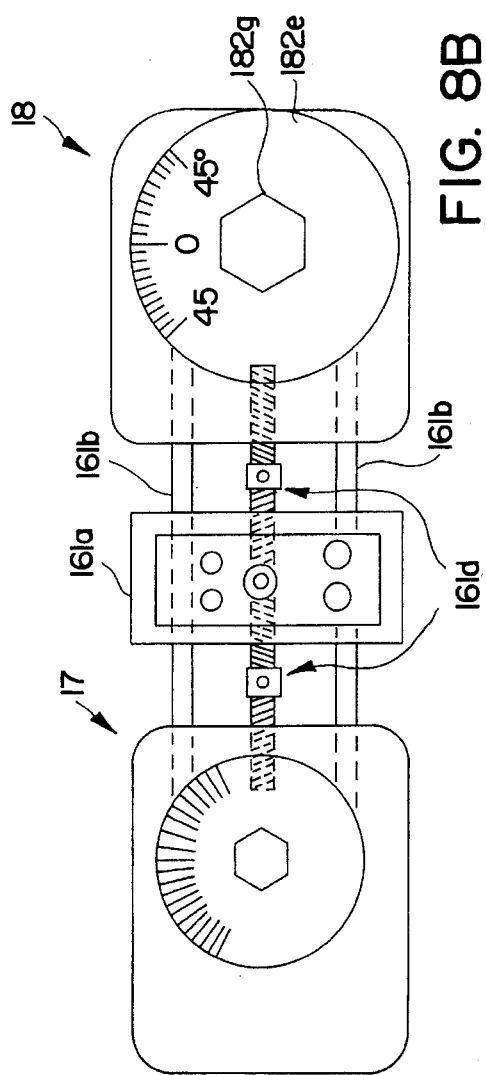
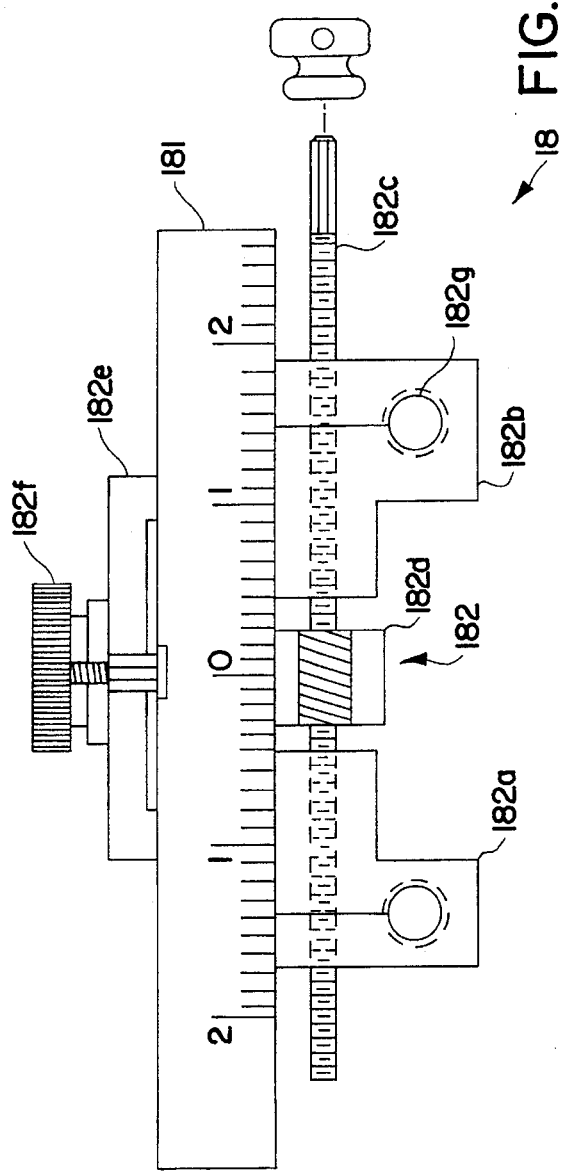

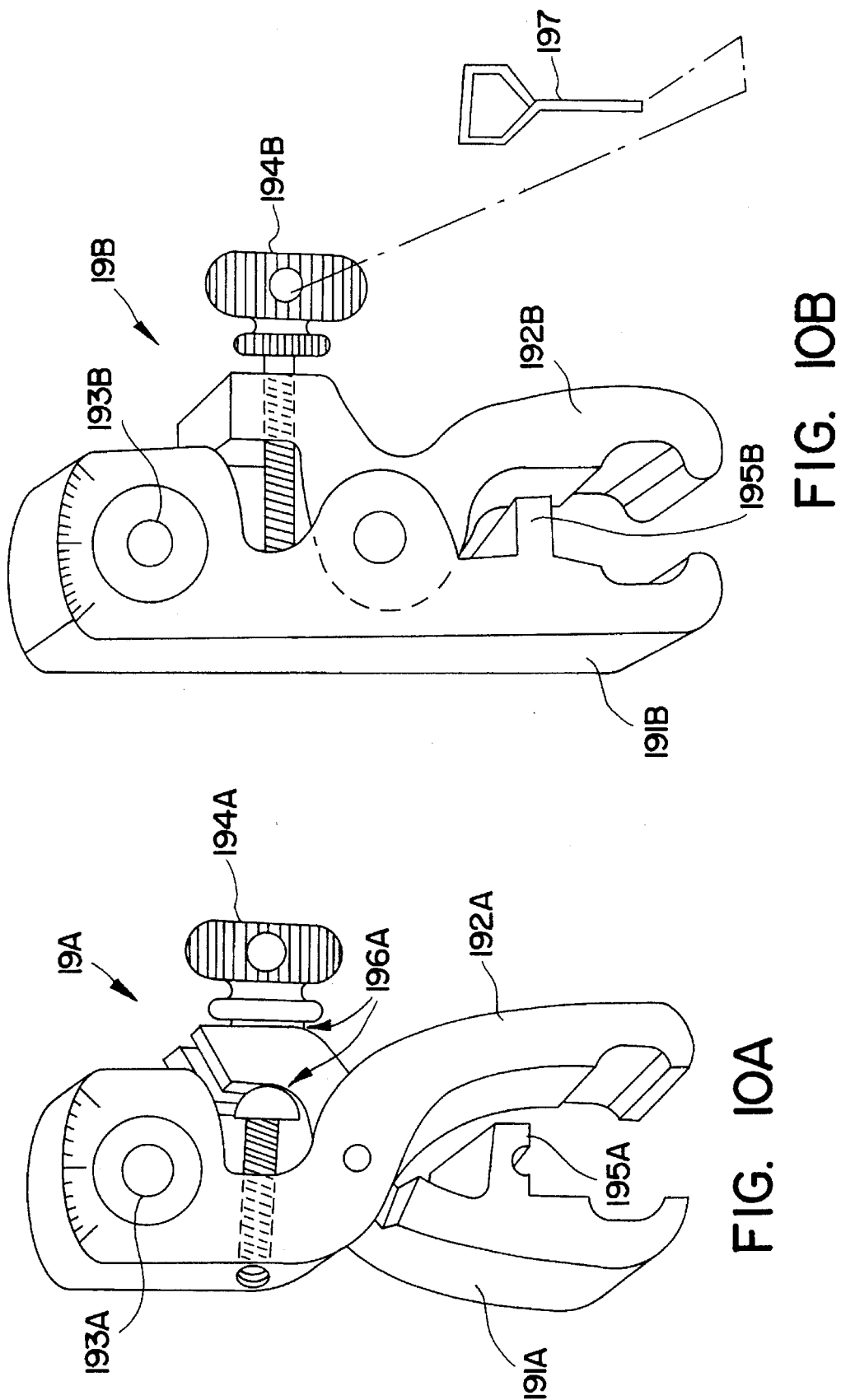

ASSEMBLY TOOL FOR ASSEMBLING A MANDIBULAR DISTRACTION DEVICE

BACKGROUND OF THE INVENTION

The present invention relates generally to the correction of deficiencies in mandibular growth. More specifically, the present invention relates to a method of mandibular distraction osteogenesis for correcting deficiencies in mandibular growth. The invention further relates to a device for use in the method of distracting the mandible as well as a laboratory assembly tool used to assemble the mandibular distraction device.

Deficiencies in mandibular growth which lead to characteristic protrusions of the maxillary teeth and deficiencies of the chin are quite common in American and Northern European populations. Data from recent large scale U.S. Public Health Service surveys of the occlusion of children and youth ages 6 through 10 indicate that about 20 percent of the U.S. population has mandibular deficiency, and about 5 percent of the total U.S. population has skeletal mandibular deficiency (deficiency in the growth of the lower jaw) so severe that the only way to correct such deficiency is to perform a total mandibular (lower jaw) resection (osteotomy) and to advance the lower jaw to a more favorable forward position.

A total mandibular osteotomy, or a sagittal split osteotomy, is a major surgical procedure that can have many complications. In this procedure, as illustrated in FIG. 1, a human mandible is split at opposite points on the mandible. The forward part of the mandible is then brought apart from the rearward part and stabilized with titanium screws at point S as labeled in the figure. The forward part F is indicated in FIG. 1 by the arrows A as having been moved.

This procedure cuts the bone marrow, and is thus detrimental to the inner nerves and blood vessels of the mandible.

In addition, a total mandibular osteotomy can involve the complications of bleeding, obstruction of the airway, possible infection, neurological problems such as possible paralysis of the inferior alveolar nerve and loss of sensation to the lip, failure of intermaxillary fixation (stabilization of the mandible after surgery), relapse-movement of the lower jaw in the direction from which it was advanced, and possible displacement of the temporo-mandibular jaw joints during the surgery.

Needless to say, such surgery requires a hospital stay, and many patients are reluctant to agree to this. Further, total treatment time is on the order of 30 months.

The other 15 percent of mandibular deficiencies are less severe, and if they are caught early, during the pubertal growth stage, are amenable to conventional orthodontics (braces) or a combination of orthodontics and functional appliance treatment. However, functional appliances are of most benefit to a patient when the patient is undergoing body and jaw growth. But most researchers are not convinced that functional appliances can and do stimulate more mandibular growth than the mandible was meant to grow genetically.

A process of lengthening human long bones has been utilized for the past 40 years. This process was designed by a Russian surgeon, Dr. Gavriel A. Ilizarov. The principles of the method of Dr. Ilizarov are presented in an article based on a speech delivered by Dr. Ilizarov on Oct. 30, 1987 at the annual Scientific Program of the Alumni Association and material presented by Dr. Ilizarov at a three day international conference on the Ilizarov techniques for the management of difficult skeletal problems.

SUMMARY OF THE INVENTION

The object of the present invention is to provide an appliance or device for distraction osteogenesis that is applicable to the five percent of severe cases requiring surgery as well as to the less severe 15 percent of cases if those cases have missed their opportunity for orthodontic/functional correction during their pubertal growth years. Distraction osteogenesis is, by definition, the process of generating new bone by stretching. Thus, it is the more specific object of the present invention to provide a method and apparatus for generating new mandibular bone by stretching the mandible.

It is a further object of the invention to provide a device which will orthodontically lengthen the mandible while minimizing the extent of the conjunctive lower jaw surgery.

It is a further object of the present invention to provide a tool for use in the laboratory for assembling or constructing the mandibular distraction osteogenesis device of the present invention.

Initially, the objects of the present invention are met by the provision of a method of mandibular distraction osteogenesis. This method involves performing corticotomy surgery at two points on opposite sides of the mandible. An expansible distraction device is attached to the teeth of the mandible on opposite sides of the two points of the corticotomy surgery, and the expansible distraction device is then periodically expanded until a desired mandibular length is attained.

The method further comprises preparing the expansible distraction device for attachment during the corticotomy surgery. This includes fitting a plurality of bands onto the teeth of the mandible, taking an impression of the teeth of the mandible, removing the bands from the teeth of the mandible and placing the bands in the impression, preparing a solid model of the teeth of the mandible from the impression, the bands being located on the solid model, and then attaching the expansion screw devices to the bands.

Preferably, four expansion screw devices are attached to eight bands fitted onto the teeth of the mandible in the step of fitting, including two bicuspid and two molar bands on each side of the mandible.

The impression is preferably an alginate impression that is poured up with dental stone or plaster. The expansion screw devices are preferably soldered to the bands.

The expansible distraction device is expanded in the desired direction of the distraction of the mandible. The screw devices separate the bands on each side of the mandible from each other at the point of the corticotomy surgery on the mandible. Preferably, the expansible screw devices are expanded at a rate of 1 mm per week.

The objects of the present invention are further met by the provision of a mandibular distraction device having first and second sets of tooth bands, a first pair of expansible screw devices connected to the first set of tooth bands and a second pair of expansible screw devices connected to the second set of tooth bands.

Each expansible screw device preferably comprises first and second body portions that have aligned threaded holes extending therein and a threaded shaft engaging both of the threaded holes.

Further, each set of tooth bands is preferably disposed along a respective tooth line, each expansible screw device of each pair of expansible screw devices being disposed on a side of the tooth line opposite the other expansible screw device of the pair. Each pair of expansible screw devices is soldered to their respective set of tooth bands.

Further, each set of tooth bands preferably comprises a plurality of bands that are aligned for disposition on the teeth of one side of the mandible. Each screw device has a forward portion that connects to some of the bands on one set of tooth bands and a rearward portion connected to the remainder of the bands of the set. The forward and rearward portion are thus expansible relative to each other for separation of the bands from each other.

Preferably, the first set of tooth bands, having the first set of expansible screw devices thereon, is connected to the second set of tooth bands, having the second set of expansible screw devices thereon, at forward portions of the expansible screw devices. If so desired, the forward portions of the expansible screw devices can be connected to each other by a fifth expansible screw device.

The objects according to the present invention are further met by an appliance assembly tool for assembling the mandibular distraction device. This tool has a base having a vertical support arrangement thereon. A mandibular model holding device is connected with the base for holding a mandibular model. A clamp assembly is vertically movably mounted on the base about the holding device, with the clamp assembly being mounted on the base by the vertical support arrangement. The clamp assembly comprises first and second clamp supports that are adjustably mounted with respect to the vertical support arrangement, and has at least one clamp adjustably mounted on each clamp support.

The vertical support arrangement comprises a rigid post that is mounted on the base, with a slider vertically slidable on the rigid post, and a rigid bar connected to the slider. The clamp assembly is supported by the rigid bar. Further, the clamp assembly may be connected to the rigid bar by an adjustable ball and socket joint.

The mandibular model holding device preferably comprises a spring loaded clamp positioned below the clamp assembly. The spring loaded clamp may comprise a fixed bar that is fixed to the base, and a moveable bar that is spring biased toward the fixed bar. The fixed and moveable bars define a space therebetween for receiving the mandibular model.

Alternatively, the spring loaded clamp of the mandibular model holding device can comprise a first holding bar that is horizontally adjustably connected to the base and a second holding bar that is biased toward the first holding bar. The first and second holding bars define a space therebetween for receiving the mandibular model.

The clamp assembly further comprises an adjustable connection that connects the first and second clamp supports for adjustment thereof toward and away from each other. This adjustable connection may comprise a central member that has the first and second clamp supports on opposite sides thereof, with slide rods connected with the central member having the first and second clamp supports slidably mounted thereon. An adjustment mechanism adjusts the position of the first and second clamp supports along the slide rods.

Further, each clamp support comprises a first member that is connected with the adjustable connection and a second member that is pivotably mounted on the first member, the clamp being mounted on the second member.

The second member may comprise first and second clamp support members that are adjustably connected to each other for movement toward and away from each other. The at least one clamp preferably is two clamps that are mounted on respective clamp support members, so that the two clamps are pivotable together through the second member being pivotably mounted on the first member and adjustable relative to each other.

Further, each clamp is pivotably mounted to a respective clamp support member for pivotable movement about an axis that is substantially perpendicular to the axis about which the second member is pivotably mounted on the first member.

Thus, each of the first and second clamp supports preferably has two clamps thereon, each of the first and second clamp supports comprises a means for adjusting a fixed position of the clamps thereof such that the clamps are pivotable together about a first axis, are moveable toward and away from each other in a direction substantially perpendicular to the first axis and are individually pivotable about a second axis that is substantially perpendicular to the first axis and the direction.

Furthermore, each clamp preferably comprises a pair of clamping jaws that are pivotably connected to each other. Also, the clamp assembly preferably comprises a means for adjusting the spacing between the first and second clamp supports.

Through the employment of the method of mandibular distraction osteogenesis according to the present invention, and the use of the mandibular distraction device according to the present invention, assembled by the appliance assembly tool according to the present invention, a number of advantages may be achieved. As noted above, the invention will orthodontically lengthen the mandible while minimizing the extent of the conjunctive lower jaw surgery.

Further, the invention will improve the facial profile by advancing or lengthening the deficient mandible. This will improve the lip balance, lip competence, and lip seal. This will also help to eliminate mouth breathing pattern problems. Further, incisor guidance and function will be established.

The invention will also reduce the orthodontic-surgical treatment time. Treatment time can be expected to be reduced to on the order of 12 months, instead of 30 months as with the prior art sagital split osteotomy surgery.

The invention will also bring the mandible forward, thus bringing the tongue forward and diminishing chances for obstructive sleep apnea or snoring. Such correction will also help to prevent class II mandibular deficiency/malocclusion. The invention will help to correct unilateral cross bites and the mandibular midline.

Further, the invention will minimize damage to the periosteal and endosteal blood supply by performing a corticotomy only, rather than a complete osteotomy as is now performed with the sagital split osteotomy surgery. This will minimize swelling and post-surgical complications, and requires no hospital stay. Further, the procedure will be far less expensive than the conventional mandibular osteotomy surgery.

BRIEF DESCRIPTION OF THE DRAWINGS

The present invention will be described in detail below with reference to the accompanying drawings, in which:

FIG. 6 is a partially exploded perspective view of a base and mandibular model holding device of the assembly apparatus of FIG. 5;

FIG. 7 is a partially exploded front view of a clamp assembly and vertical support arrangement of the assembly apparatus of FIG. 5;

FIG. 8A is a top of view of a clamp support and adjustable connection arrangement of the clamp assembly of FIG. 7;

FIG. 8B is a top view similar to FIG. 8A showing a variation thereof;

FIG. 9A is a front view of a clamp support of the assembly apparatus of FIG. 5;

FIG. 10A is a perspective view of a first embodiment of a clamp employed in the assembly apparatus of FIG. 5;

FIG. 10B is a perspective view of a second embodiment of a clamp for use with the assembly apparatus of FIG. 5;

DETAILED DESCRIPTION OF THE PREFERRED EMBODIMENTS OF THE INVENTION

Figure 1:
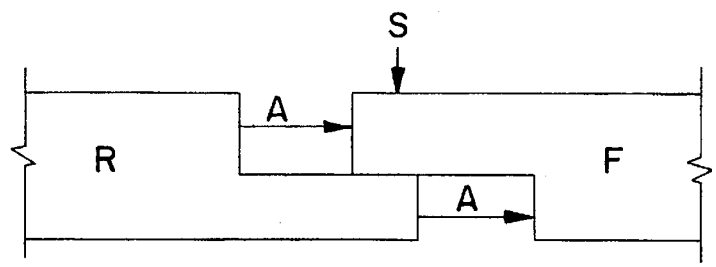
FIG. 1 is a schematic drawing illustrating sagital split osteotomy surgery.

A detailed description of the present invention will now be presented with reference to the accompanying drawing figures. In the various figures, the same reference numerals are used for similar elements throughout. The description of the invention will first proceed with the description of a mandibular distraction osteogenesis device, and then the method of mandibular distraction osteogenesis will be described. Then, an appliance assembly tool employed in the assembly of the mandibular distraction device will be described.

Figure 2:
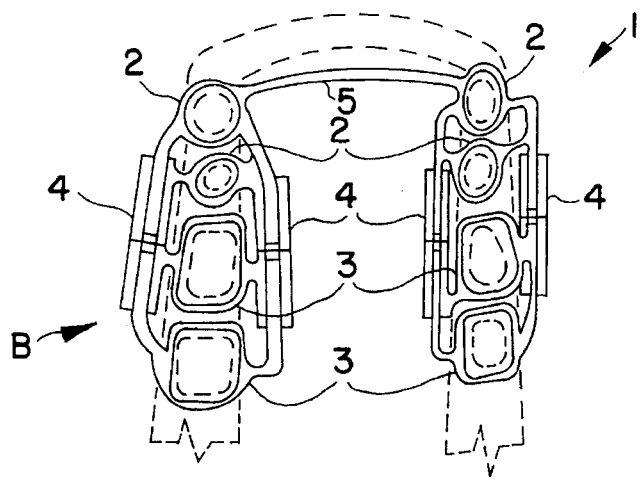
FIG. 2 is a top view of a mandibular distraction osteogenesis device according to the present invention.

Turning to FIG. 2, there is illustrated a mandibular distraction osteogenesis device 1 usable in distracting the mandible. Initially, the device 1 includes a plurality of bands for placement on the teeth of the mandible of a patient to undergo distraction osteogenesis. Preferably there are provided a total of eight bands, with two bicuspid and two molar orthodontic bands being provided for each side of the mandible, as illustrated in FIG. 2. The bands are indicated by reference numbers 2 for the bicuspid bands and reference numbers 3 for the molar bands. The mandible and the relevant teeth are schematically illustrated by a dashed line in FIG. 2.

A plurality of universal expansion screws 4 are soldered onto the bands. Preferably four universal expansion screws 4 are used, with two of the universal expansion screws 4 being provided for each side of the mandible, one universal expansion screw 4 thus being placed on each side of each set of bands. As can be seen from FIG. 2, the universal expansion screws thus extend along the sides of the bands and have suitable portions thereof soldered to the respective bands. The universal expansion screws 4 are expandable to distract a forward portion of the mandible, the upper portion as seen in FIG. 2, from a rearward portion of the mandible by separating the bicuspid bands 2 from the molar bands 3.

Figure 3:
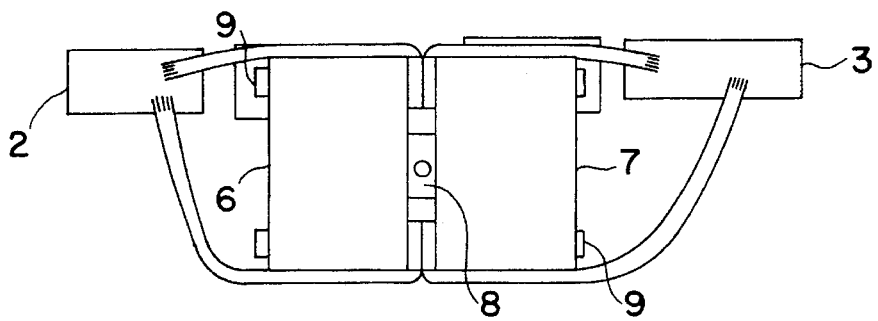
FIG. 3 is a side view of a portion of the mandibular distraction device as seen in the direction of arrow B of FIG. 2.

More specifically, and referring to FIG. 3, each universal expansion screw 4 has two halves 6 and 7 separable from each other by a screw mechanism 8. The screw mechanism 8 is a suitable mechanism rotatable between the universal expansion screw halves 6 and 7 to separate the halves from each other, such as a right and left hand threaded shaft extending into and engaging with corresponding threads in the halves 6 and 7. Suitable guide rods 9 can also extend through the halves 6 and 7 to guide the separation of the halves 6 and 7 from each other. As can be seen, suitable connecting portions are provided for connecting the halves 6 and 7 to the respective bands 2 and 3. Such connecting portions can take the form of appropriate metal wires or bars. The universal expansion screw 4 can be of the type illustrated in U.S. Pat. No. 4,482,318, for example, or could be of the type shown in U.S. Pat. No. 4,571,177, suitably adapted to the present situation. These patents are incorporated herein by reference.

By the above construction there is formed two separate portions of the mandibular distraction device 1, one portion being located on each side of the mandible. These portions are preferably connected to each other by a suitable connecting wire or bar 5, as illustrated in FIG. 5. However, note that in place of the connecting wire or bar 5, an additional, smaller, universal expansion screw 4 could be provided and incorporated into the device 1, the universal expansion screw connecting the two sides of the device 1 at the forward portions thereof in order to allow for lateral mandibular expansion, in addition to mandibular distraction or elongation.

As can be seen from FIG. 2, the bicuspid bands 2 on each side of the mandible are connected to the forward portions or halves 6 of the universal expansion screws 4, and the molar bands 3 are connected to the rear portions or halves 7 of the universal expansion screws 4. Thus, a unitary forward portion is expansible in a forward direction relative to two separate lateral portions on opposite sides of the mandible for elongation or distraction of the mandible.

Figure 4:
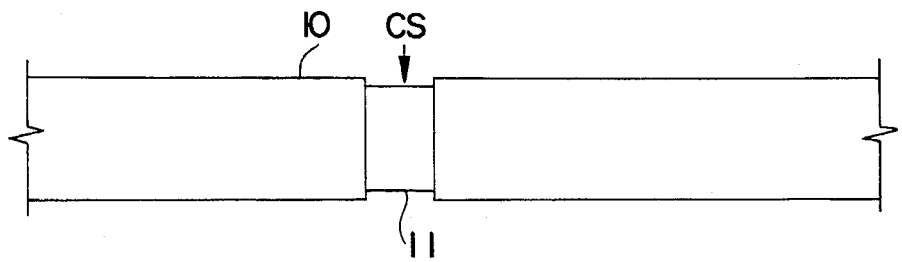
FIG. 4 is a schematic representation of corticotomy surgery as employed in the method according to the present invention.

The method of mandibular distraction osteogenesis according to the present invention is as follows. Referring to FIGS. 2–4, first two bicuspid and two molar orthodontic bands are fitted onto the respective teeth of a patient's mandible on each side of the mandible. Thus, a total of eight bands are fitted onto the teeth of the patient. An alginate impression is then taken of the patient's mandible with the bands in place. The bands are then removed and placed into the impression. Then, the impression is poured up with orthodontic (dental) stone or plaster, so as to form a model of the patient's mandible, with the bands in place thereon on the appropriate teeth of the mandible model.

The four universal expansion screws 4 are then soldered onto the bands as illustrated in FIG. 2. By the soldering of the universal expansion screws 4 onto the bands 2 and 3, the mandibular distraction device 1 as illustrated in FIG. 2 is formed. A suitable connection 5 may also be provided, or an additional universal expansion screw 4 may also be provided in place thereof to provide for lateral mandibular expansion. With the finished mandibular distraction device 1, the device is now ready to be cemented into the patient's mouth.

Accordingly, the mandibular distraction device is cemented into the patient's mouth during corticotomy surgery. Corticotomy surgery is the cutting of the outside layer (cortex) only of the mandible. Referring to FIG. 4, a section of a patient's mandible is schematically illustrated. Portion 10 represents the outer layer of the bone, i.e. the cortex. This portion is cut during the corticotomy surgery. However the bone marrow 11 is left intact. This reduces the chance of the nerves or the blood vessels being severed. The location of the corticotomy surgery is represented in FIG. 4 by the letters CS. The corticotomy surgery is performed at two points on opposite sides of the mandible to allow for the elongation or distraction of the forward portion of the mandible from a rearward portion thereof. In the case of FIG. 2, for example, the corticotomy would take place between the bicuspids and the molars on each side of the mandible to allow for the two bicuspid bands 2 on each side to be displaced forwardly from the rear molar bands 3 with the expansion of the universal expansion screws 4. Appropriate x-rays can be taken of the mandible in order to determine the exact thickness of the cortex to ensure that the bone marrow 11 is not cut.

After the cementing of the distraction device 1 during corticotomy surgery, the mandible is then distracted by expanding the four universal expansion screws 4 inside of the patient's mouth. This is accomplished by rotating the screws 8 of the universal expansion screws 4 periodically to extend the forward portion of the mandible from the rearward portion thereof. This is possible because the cortex has been cut in the corticotomy surgery. The bone marrow is softer tissue and allows for elongation to take place. Both bone and soft tissue regeneration will occur during the process of expanding the universal expansion screws 4 and distracting the mandible. Preferably, the mandible is distracted at a rate of 1 mm per week until the proper mandibular length is obtained.

In order to properly locate and solder the universal expansion screws 4 relative to the bands 2 and 3 of the mandibular distraction device 1, the present invention further provides an appliance assembly tool for positioning the universal expansion screws 4 relative to the bands 2 and 3 in order to be able to properly solder the universal expansion screws to the bands.

Figure 5A:
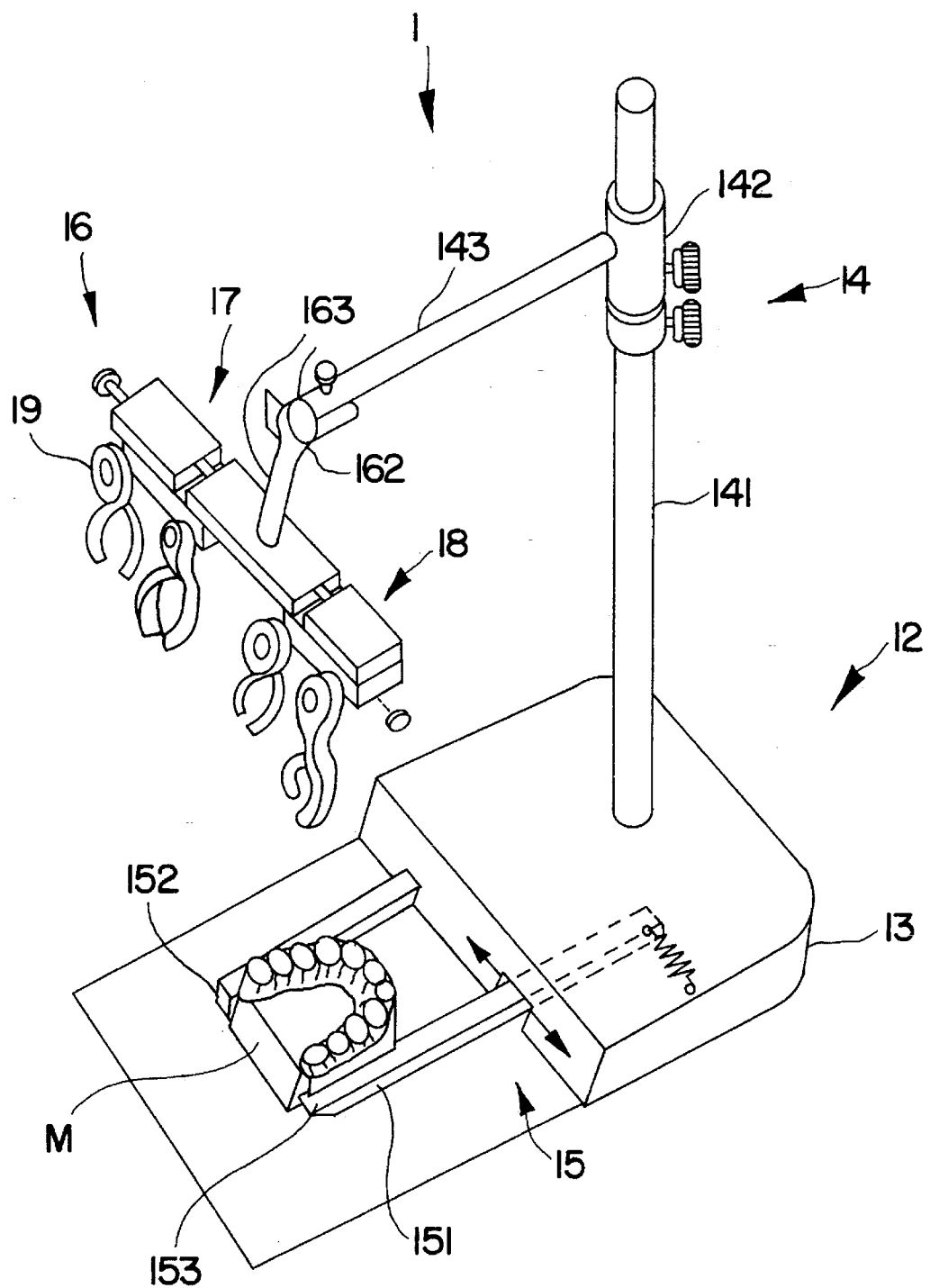
FIG. 5A is a perspective view of a first embodiment of an appliance assembly apparatus according to the present invention.

A first embodiment of the appliance assembly tool is designated by reference numeral 12 in FIG. 5A. The appliance assembly tool has a base 13 for supporting the various components thereof. A vertical support arrangement 14 is provided on the base 13 for supporting a clamp assembly 16 above a mandibular model holding device 15.

The mandibular model holding device 15 has a spring loaded clamp 151 for holding a mandibular model M in position below the clamp assembly 16. Specifically, a moveable bar 153 is spring biased in the direction of a fixed bar 152 fixed relative to the base 13 for securely holding the mandibular model M below the clamp assembly 16.

The clamp assembly 16 has first and second clamp supports 17 and 18 thereon supporting a plurality of clamps 19. The clamps 19 are used for holding the universal expansion screws 4 and positioning the universal expansion screws relative to the bands on the mandibular model M during assembly of the above-described distraction device 1.

Thus, the universal expansion screws 4 can be precisely positioned by appropriately moving the clamps 19 into position around the sides of the two sets of bands on the mandibular model M.

The vertical support arrangement 14 supports the clamp assembly 16 for vertical and pivotable movement above the mandibular model M. Specifically, a rigid post 141 is provided on the base 13 and fixed thereto. A slider 142 is vertically slidable on the rigid post 141 and can be fixed thereon with a thumb nut as illustrated in FIG. 5A. The slider 142 has a slidable support collar to help fix the position of the slider, the support collar also having a thumb nut thereon and positioned immediately below the slider as seen in FIG. 5A. Connected to the slider 142 is a rigid beam or bar 143 for supporting the clamp assembly 16.

The clamp assembly 16 is connected to the rigid bar 143 by a lifter bar 163 of the clamp assembly that is connected to the rigid bar 143 by a ball and socket joint 162. The lifter bar 163, for example, can have a ball on the end thereof located in a suitable socket connected with the rigid bar 143. The socket can, for example, comprise a suitable socket member defining a substantially spherical socket allowing for movement of the ball therein so that the lifter can be moved to different positions. The member can be appropriately connected to the rigid bar 143 by ball tighteners and a ring spring to allow for adjustable fixation of the lifter bar 163 relative to the rigid bar 143. Thus, the clamp assembly is positionable in different positions relative to the rigid bar 143 through the ball and socket joint 162. See also FIG. 7.

Figure 5B:
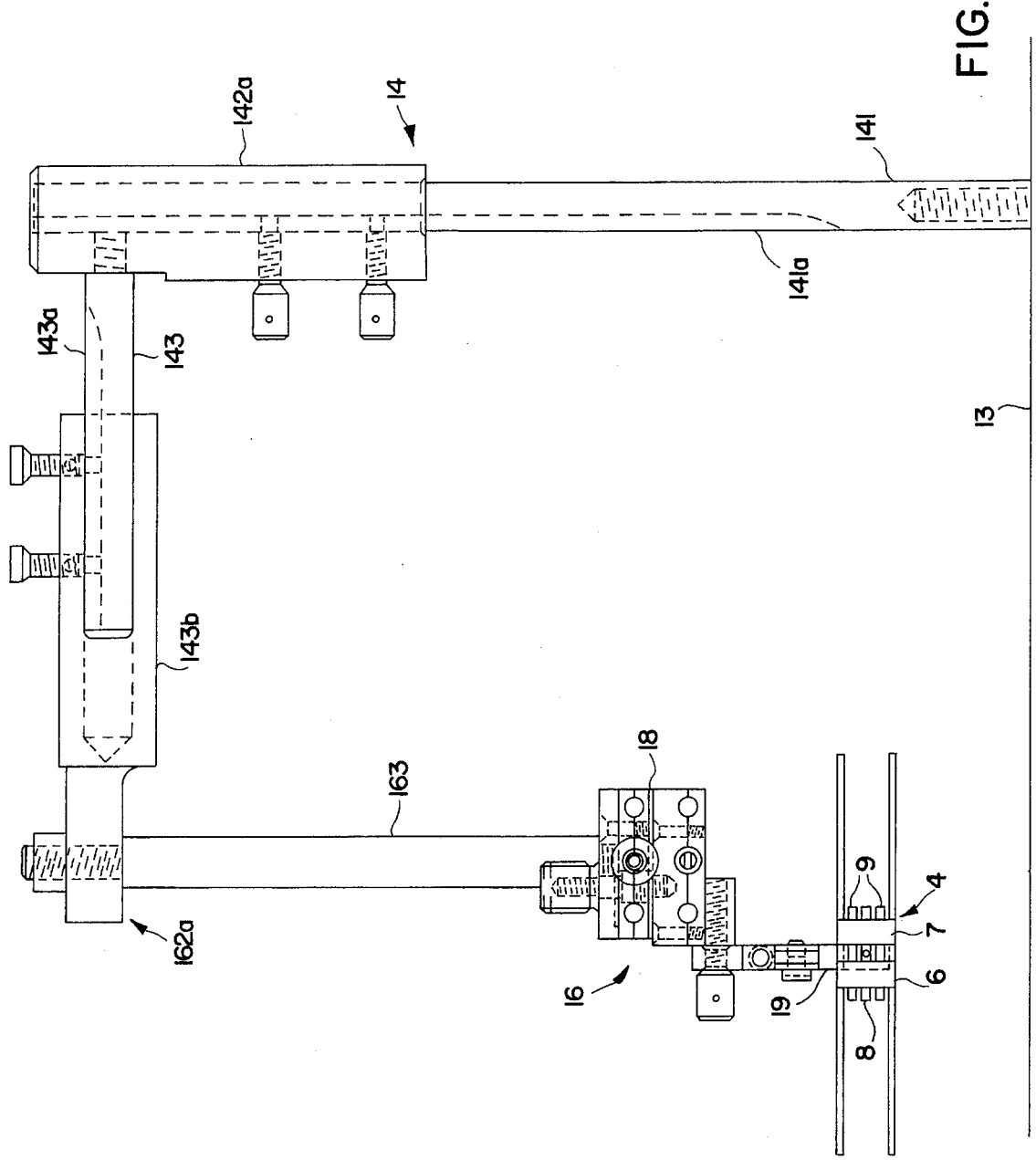
FIG. 5B is a side view of a second embodiment of an appliance assembly apparatus according to the present invention.

FIG. 5B represents a second embodiment of the appliance assembly tool according to the present invention. For the sake of brevity, only the distinctions between this embodiment and the embodiment described above will be described. In this embodiment, the rigid post 141 is provided with a groove or channel 141a. A slider 142a is slidable along the groove or channel 141a and fixable therein with the illustrated screws. The rigid bar 143 is connected to the slider 142a, and has a similar channel or groove 143a cut therein. A second portion 143b of the rigid bar 143 receives the portion of the rigid bar 143 having the channel 143a therein. The rigid bar 143 can thus be elongated or shortened as desired, and fixed with the two illustrated screws. In addition, in this embodiment, instead of a ball and socket joint connecting the rigid bar 143 to the clamp assembly 16, a simple threaded connected 162a is employed, as illustrated.

Figure 5C:
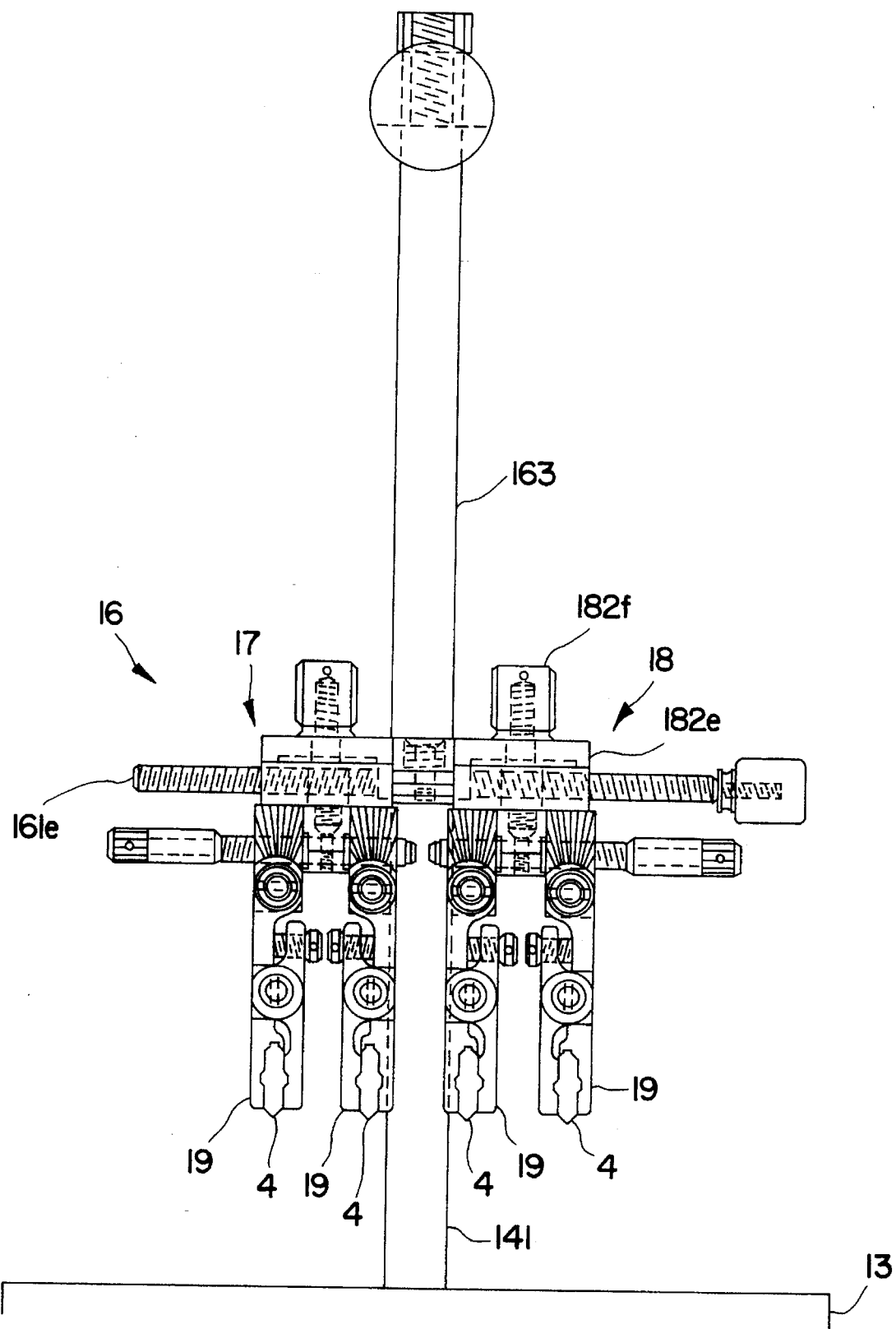
FIG. 5C is a front view of the second embodiment of the appliance assembly apparatus.

Further note FIG. 5C, which illustrates the second embodiment of the appliance assembly tool 12 from a front view thereof. Various details of the clamp assembly 16 can also be seen in these figures, which will be further explained below.

An alternative arrangement of the base 13 and the mandibular model holding device 15 is illustrated in FIG. 6. In this figure, first and second holding bars 152a and 153a are provided on respective sides of a space defined between two portions of the base 13. The bars 152a and 153a are connected with the base 13 by appropriate hex shoulder bolts, as illustrated, to be loosely mounted on each side of the space. A set screw is inserted between the hex shoulder bolts, and a spring is mounted behind each of the bars 152a and 153a to provide a light spring pressure thereon so that the two bars can hold the mandibular model M therebetween.

FIG. 7 is a front view of the clamping assembly 16. This figure more specifically illustrates the ball and socket joint 162, the rigid bar 143, the slider 142 with the thumb nuts 142b and 142c, and the support collar 142a mounted on the rigid post 141. Further, the figure also illustrates the first and second clamp supports 17 and 18. As can be seen from the figure, each clamp support supports two clamps 19 thereon. The first and second clamp supports 17 and 18 are connected to each other through an adjustable connection 161.

The adjustable connection 161 is provided to allow adjustment between the first and second clamp supports 17 and 18 in a direction substantially perpendicular to the lifter bar 163. More specifically, the adjustable connection 161 provides for a proper spacing between the two sets of clamps for the appropriate width of the mandibular model M held in the holding device 15. Thus, the two sets of clamps can be adjusted to an appropriate separation for the distance between the two sides of the mandible. The adjustable connection 161, referring to FIGS. 8A, 8B and 11, comprises a central member 161a having a suitable connection for the lifter bar 163, such as a threaded coupling. Extending through and preferably fixed to the central member 161a are slide rods 161b for guiding the first and second clamp supports 17 and 18 in sliding movement relative thereto. In the embodiment in FIG. 8A, a shaft 161c is rotatably mounted in the central member 161a and has opposite ends thereof provided with oppositely directed threads thereon for threadedly engaging respective ones of the first and second clamp supports 17 and 18. Thus, rotation of the knob at the end of the shaft 161c will cause the first and second clamp supports 17 and 18 to either separate or approach each other, depending on the direction of turning. An alternative arrangement is illustrated in FIG. 8B. Here, separate screw shafts 161d are provided between each of the first and second clamp supports 17 and 18 and the central member 161a. Each of these shafts has oppositely directed threads thereon engaging, on one side, the central member, and on the other side, the respective clamp support. A central portion of each shaft 161d is provided with at least one hole extending therethrough for insertion of an appropriate tool for turning the shafts in adjustment. Thus, in the arrangement of FIG. 8B, the first and second clamp supports are separately adjustable relative to central member 161a.

Figure 11:
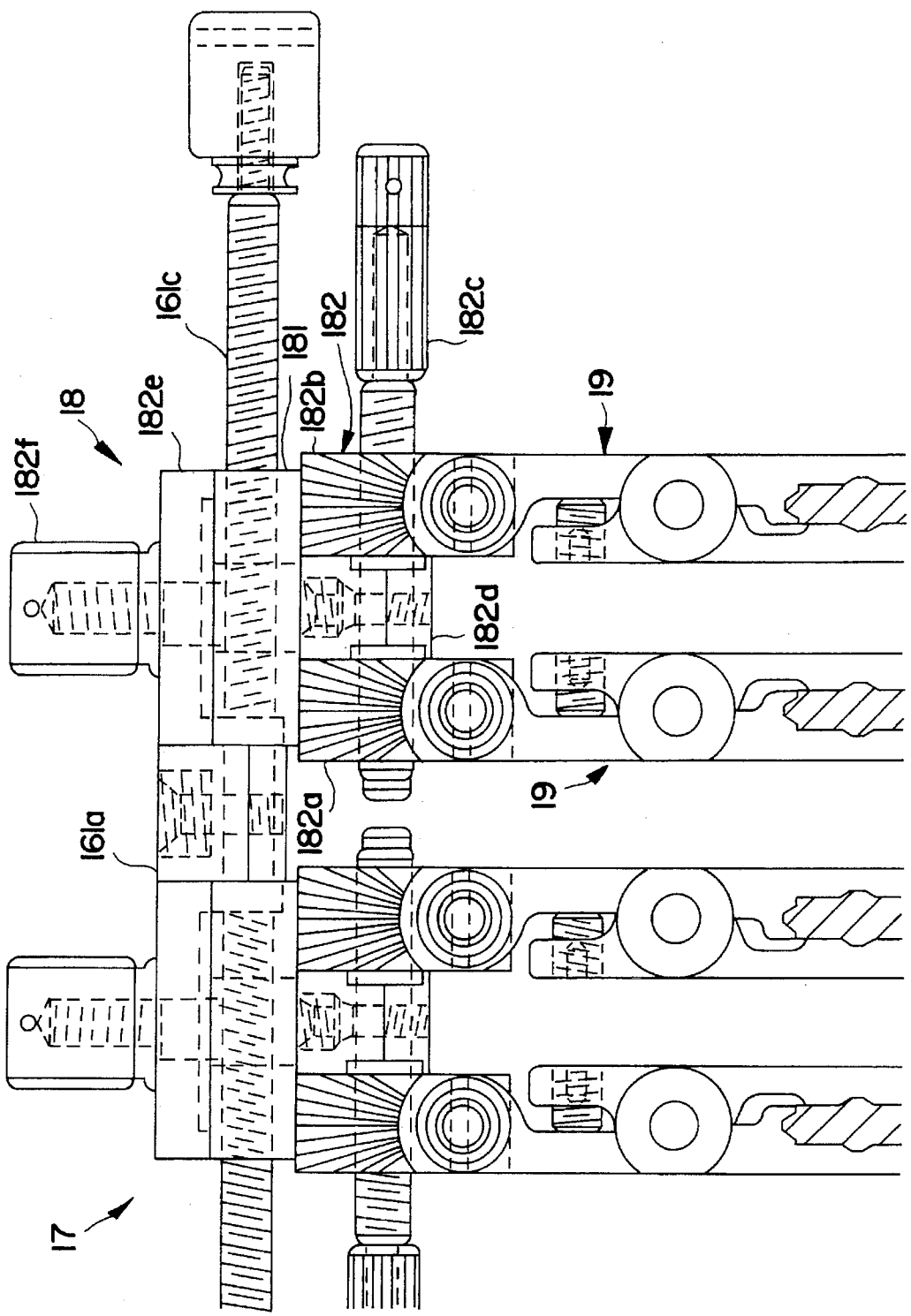
FIG. 11 is a front view of the clamp assembly according to the present invention.

The first and second clamp supports 17 and 18 are substantially similar, and thus only the second clamp support 18 will be described in conjunction with FIG. 9A and FIG. 11. In this figure, it can be seen that the second clamp support 18 comprises essentially two parts or members. A first member 181 is connected with the adjustable connection 161, as discussed with respect to FIGS. 8, but the connection is not specifically illustrated in FIG. 9A. Two clamp support members 182a and 182b are provided on the underside of the first member 181. Each clamp support member has a suitable threaded portion for engagement with a threaded shaft 182c. The shaft 182c has a thumb turn pressed on a narrowed end thereof for turning the shaft 182c. The shaft 182c is rotatably mounted in a member 182d but is axially fixed relative to the member 182d. Thus, rotation of the shaft 182c, having the threads thereon directed in opposite directions on opposite sides of the member 182d, will adjust the relative position of the clamp support members 182a and 182b. Thus, the spacing between clamps connected to the clamp support members can be adjusted by the rotation of the shaft 182c. A scale is provided on the first member 181 for precisely determining and fixing the separation between the clamps. For purposes of mounting the clamps, suitable openings 182g are provided in the clamp support members 182a and 182b.

The second member 182 further includes a degree disk 182e on the upper surface of the first member 181. This degree disk can also be seen from FIG. 8A or FIG. 8B. The degree disk 182e is keyed to and turned by a knob 182f. Thus, the degree of rotation of the disk 182e can be determined by reference to the upper surface thereof with respect to a mark indicated on the upper surface of the first member 181, as can be seen from FIG. 8A. Rotation of the degree disk 182e also causes rotation of the member 182d, as they are connected together for rotation. Thus, the angular position of the two clamps can be precisely adjusted by appropriate rotation of the degree disk 182e on each clamp support.

The scale on the first member 181, as well as the two zero lines indicated on the clamp support members 182a and 182b are preferably laser scribed lines. The clamp support members 182a and 182b, also preferably include suitable guide rods for guiding the movement thereof in a manner similar to the guiding of the movement of the first and second clamp supports 17 and 18.

Figure 9B:
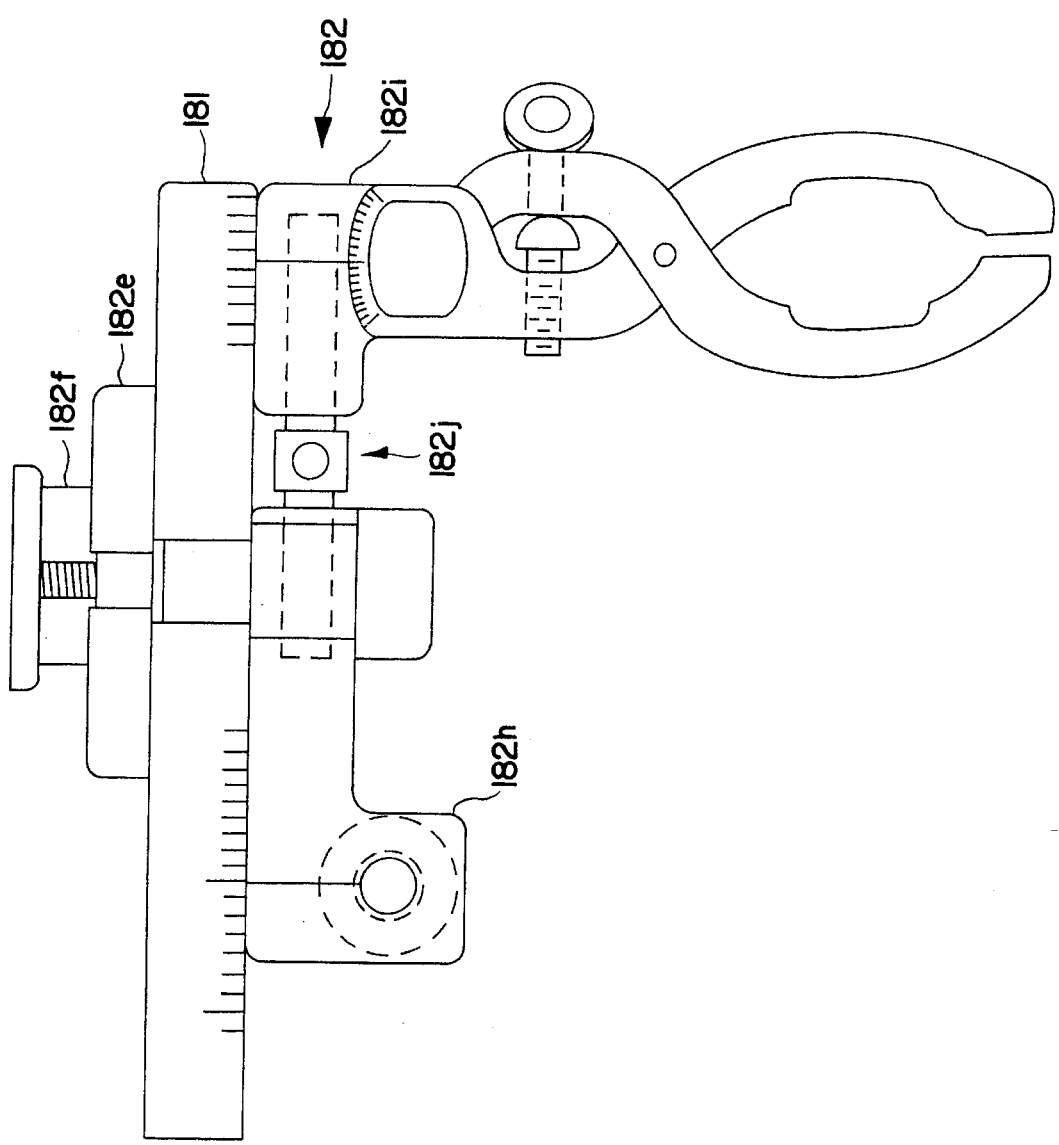
FIG. 9B is a front view of an alternative arrangement of a clamp support.

FIG. 9B illustrates an alternative arrangement of the second clamp support 18. In this arrangement, one clamp support member 182h is keyed or fixed to the shaft or axis of the degree disk 182e, and the other clamp support member 182i is moveable relative thereto by a suitable adjustment mechanism 182j. The shaft of the degree disk 182e can have a hexagonal shape engaging with the degree disk 182e, be rotatable in the first member 181 and have another hexagonal shape engaging the clamp support member 182h. As can also be seen in this figure, the clamps can be mounted to their clamp support members so as to be adjustable about an axis substantially perpendicular to the plane of the paper as seen in FIG. 9B. This axis is also substantially perpendicular to the axis of the shaft of the degree disk 182e. Thus, precise angular positioning of the clamps can take place for precise positioning to the universal expansion screws 4.

Two clamps 19a and 19b can be further seen from FIGS. 10A and 10B, respectively. Referring first to FIG. 10A, the first example of a clamp 19a includes first and second clamp halves 191a and 192a pivotably connected to each other by a fine screw at a pivot point thereon. In this example, cut out notches are provided on the clamp halves so that they can fit together for relative pivotable movement therebetween. Further, a clamp screw 194a is provided threaded into the clamp half 192a and holds the other clamp half 191a between two rolling surfaces 196a. By adjusting the threaded position of the screw 194a, for example with the tool 197 illustrated in FIG. 10b, the relative position of the two clamps halves to each other can be adjusted. The universal expansion screws 4 are mounted in the clamps in the illustrated notches, and are further positioned by suitable palatal expansion screw locators 195A. A wedge screw opening 193a is provided for a suitable wedge screw for mounting the clamp to its respective clamp support member. The degree lines illustrated at the top of the clamp above the opening 193A allows for a precise determination of the angular position of the clamp on its respective clamp support member. Also note FIG. 9B.

FIG. 10b provides a slightly modified arrangement of the clamp 19, wherein the two clamp halves do not cross each other as in FIG. 10A. Here, the clamp screw 194B is threadedly engaged with the clamp half 192B, and rotation thereof pivots the clamp half 192b relative to the clamp half 191B.

Figure 12C:
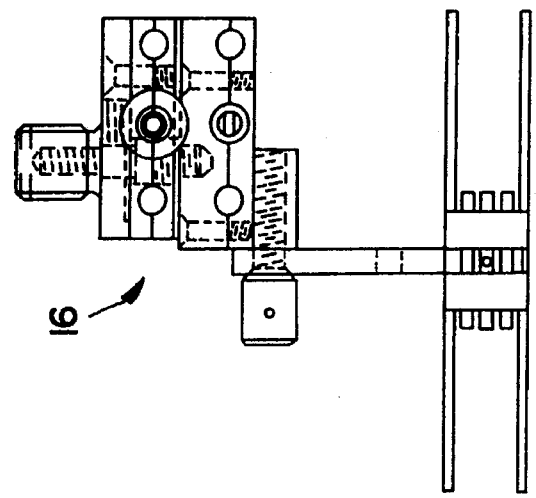
FIGS. 12A–12C are top, front and side views, respectively, of the clamp assembly of the present invention in a closed position.
Figure 12A:
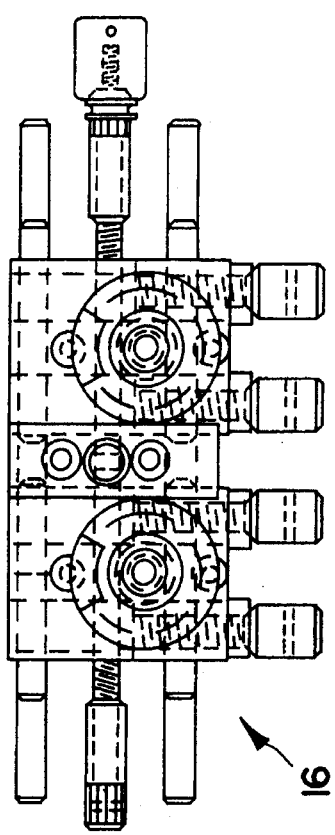
Figure 12B:
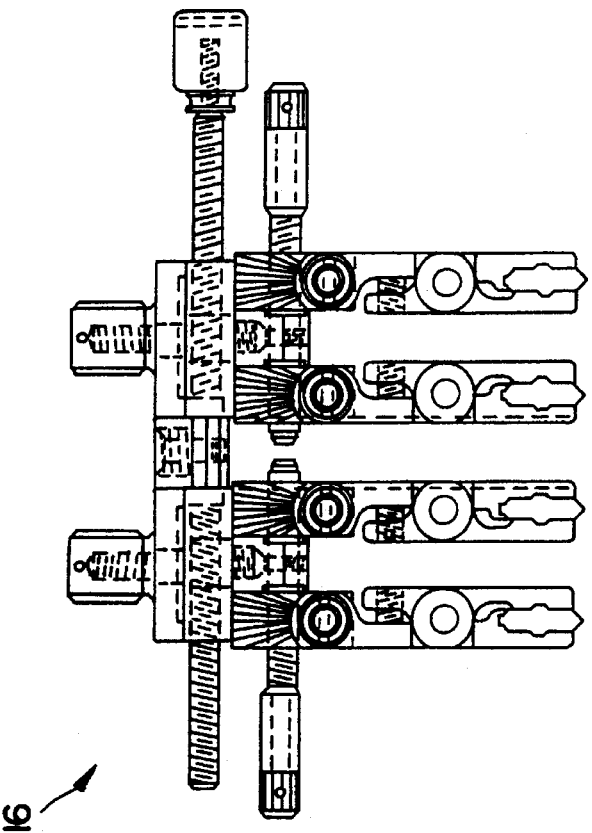
Figure 13C:
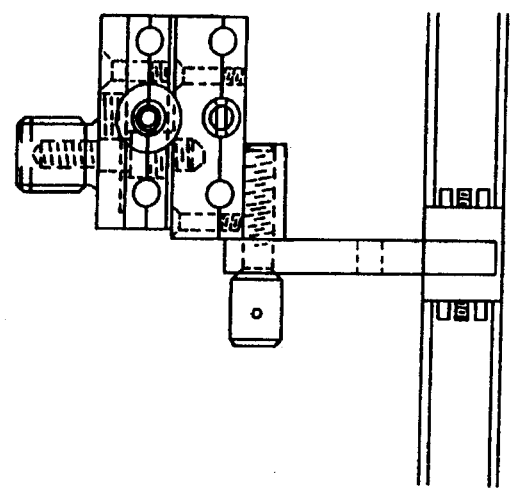
FIGS. 13A–13C are top, front and side views, respectively, of the clamp assembly according to the present invention in an open position.
Figure 13A:
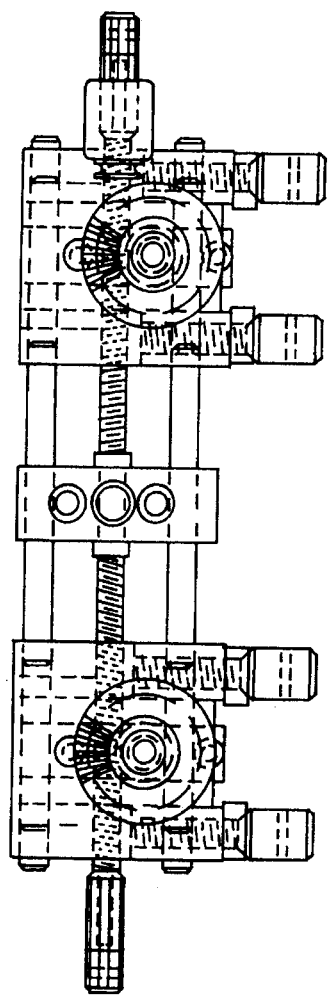
Figure 13B:
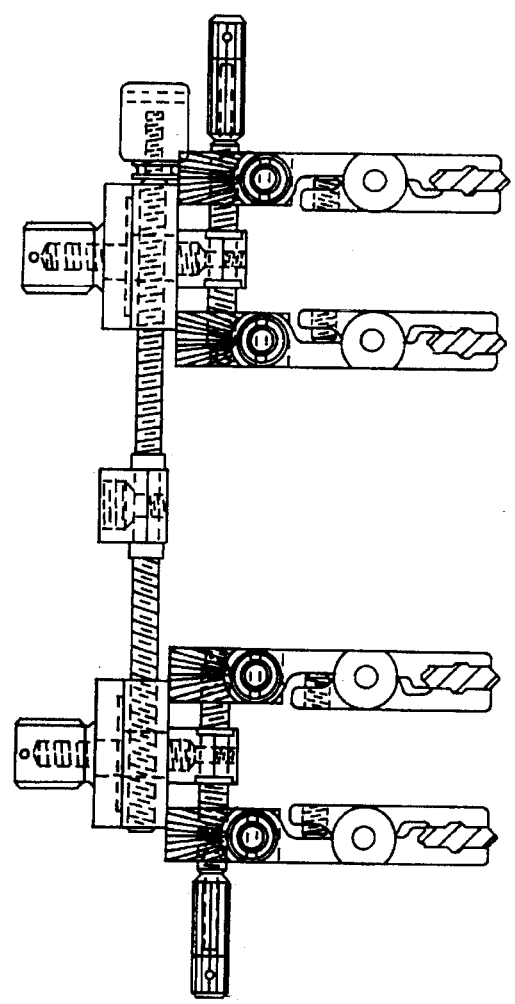

FIGS. 12 and 13 are provided to illustrate two different positions of the clamp assembly 16 according to the present invention. In FIGS. 12, the position wherein the clamp supports 17 and 18 and the clamps 19 are as close to each other as possible is illustrated. On the other hand, in FIGS. 13, the clamp supports 17 and 18 are illustrated as substantially separated from each other, as are the clamps 19.

It will be understood that the appliance assembly tool according to the present invention can be suitably formed out of many different types of materials. Preferably, however, the primary components of the tool are formed of suitable metals that are subject to precise manufacturing operations so as to result in a high precision tool. Appropriate aluminum or steel, or zinc with yellow chromate, or brass, may be contemplated. However, it should be understood that many different types of materials may be used for the components of the tool as long as they are capable of resulting in a sufficiently precise tool.

Referring again to FIG. 5A, it can be seen that the clamp assembly 16 as a whole is adjustable vertically on the rigid post 141, angularly about the axis of the rigid post 141 due to the rotation of the slider 142 as desired, and is also adjustable through the ball and socket joint 162. Furthermore, the first and second clamp supports 17 and 18 are linearly adjustably relative to each other to appropriate positions thereof spacing the two sets of clamps from each other. Referring to FIGS. 9, each set of clamps on each clamp support are rotatably adjustable about an axis perpendicular to the direction of adjustment relative to the other clamp support. Further, the two clamp support members of each clamp support are linearly adjustable relative to each other for a proper spacing between the two clamps 19 thereof. Further, each of these clamps is further pivotably adjustable about an axis perpendicular to direction of adjustment between the clamp support members as well as being perpendicular to the direction of the axis of rotational adjustment of the clamp support members. Thus, the universal expansion screws 4 can be carefully and precisely positioned relative to the bands 2 and 3 on the mandibular model M when soldering the universal expansion screws 4 thereto.

While preferred embodiments of the present invention have been described above in some particularity, the scope of the present invention should not be limited thereby, as various modifications thereof will be apparent to those of skill in the art.

I claim:

1. An appliance assembly tool, comprising:
a base having a vertical support arrangement thereon;
a mandibular model holding device connected with said base for holding a mandibular model;
a clamp assembly vertically movably mounted on said base above said holding device, said clamp assembly being mounted on said base by said vertical support arrangement, and said clamp assembly comprising first and second clamp supports adjustably mounted with respect to said vertical support arrangement and at least one clamp adjustably mounted on each said clamp support;
wherein said clamp assembly further comprises an adjustable connection connecting said first and second clamp supports for adjustment of said first and second clamp supports toward and away from each other;
wherein said adjustable connection comprises a central member having said first and second clamp supports on opposite sides thereof, slide rods connected with said central member having said first and second clamp supports slidably mounted thereon and an adjustment mechanism for adjusting the position of said first and second clamp supports along said slide rods.

2. An appliance assembly tool, comprising:
a base having a vertical support arrangement thereon;
a mandibular model holding device connected with said base for holding a mandibular model;
a clamp assembly vertically movably mounted on said base above said holding device, said clamp assembly being mounted on said base by said vertical support arrangement, and said clamp assembly comprising first and second clamp supports adjustably mounted with respect to said vertical support arrangement and at least one clamp adjustably mounted on each said clamp;
wherein said clamp assembly further comprises an adjustable connection connecting said first and second clamp supports for adjustment of said first and second clamp supports toward and away from each other;
wherein each said clamp support comprises a first member connected with said adjustable connection and a second member pivotably mounted on said first member, said at least one clamp being mounted on said second member.

3. The appliance assembly tool of claim 2, wherein each said second member comprises first and second clamp support members adjustably connected to each other for movement toward and away from each other, and said at least one clamp comprises two clamps mounted on respective said clamp support members, wherein said two clamps are pivotable together through said second member being pivotably mounted on said first member and adjustable relative to each other.

4. The appliance assembly tool of claim 2, wherein each said clamp is pivotably mounted to a respective said clamp support member for pivotal movement about an axis substantially perpendicular to the axis about which said second member is pivotably mounted on said first member.

5. An appliance assembly tool, comprising:
a base having a vertical support arrangement thereon;
a mandibular model holding device connected with said base for holding a mandibular model;
a clamp assembly vertically movably mounted on said base above said holding device, said clamp assembly being mounted on said base by said vertical support arrangement, and said clamp assembly comprising:
first and second clamp supports adjustably mounted with respect to said vertical support arrangement so as to be adjustable to different spacings therebetween and
at least one clamp adjustably mounted on each said clamp support so as to be both pivotable and translatable relative to said clamp support.

6. The appliance assembly tool of claim 5, wherein said vertical support arrangement comprises a rigid post mounted on said base, a slider vertically slidable on said rigid post and a rigid bar connected to said slider, said clamp assembly being supported by said rigid bar.

7. The appliance assembly tool of claim 6, wherein said clamp assembly is connected to said rigid bar by an adjustable ball and socket joint.

8. The appliance assembly tool of claim 5, wherein said mandibular model holding device comprises a fixed bar fixed to said base and a moveable bar spring biased toward said fixed bar, said fixed and movable bars defining a space therebetween for receiving a mandibular model.

9. The appliance assembly tool of claim 5, wherein said mandibular model holding device comprises a first holding bar horizontally adjustably connected to said base and a second holding bar biased toward said first holding bar, said first and second holding bars defining a space therebetween for receiving a mandibular model.

10. The appliance assembly tool of claim 5, wherein said clamp assembly further comprises an adjustable connection connecting said first and second clamp supports for adjustment of said first and second clamp supports toward and away from each other.

11. The appliance assembly tool of claim 5, wherein each of said first and second clamp supports has two clamps thereon, each of said first and second clamp supports comprises means for adjusting a fixed position of said clamps thereof such that said clamps are pivotable together about a first axis, are movable toward and away from each other in a direction substantially perpendicular to the first axis, and are individually pivotable about a second axis substantially perpendicular to the first axis and the direction.

12. The appliance assembly tool of claim 5, wherein each said clamp comprises a pair of clamping jaws pivotably connected to each other.

13. The appliance assembly tool of claim 5, wherein said clamp assembly comprises means for adjusting the spacing between said first and second clamp supports.

14. An appliance assembly tool, comprising:

a base;

a mandibular model holding means for holding a mandibular model in a fixed position relative to said base;

a clamp assembly comprising first and second clamp supports, means for adjusting and setting the relative position between said first and second clamp supports, a plurality of clamps mounted on said first and second clamp supports, and means for adjusting and setting the position of said plurality of clamps relative to said first and second clamp supports to which said plurality of clamps are mounted; and vertical support and adjustment means for supporting said clamp assembly on said base such that said clamp assembly is capable of being positioned above said mandibular model holding means and capable of being adjusted relative to said mandibular model holding means such that said clamps can be vertically moved and positioned adjacent to portions of a mandibular model when said mandibular model holding means holds a mandibular model.

15. The assembly tool of claim 14, wherein each of said clamp supports has two of said plurality of clamps thereon in a pair, and said means for adjusting and setting the position of said plurality of clamps relative to said first and second clamp supports is capable of independently adjusting the angular orientation of each said pair of clamps and adjusting the spacing between each of said plurality of clamps in each said pair.

16. The assembly tool of claim 14, wherein each said clamp comprises a means for holding a member to be positioned adjacent to a portion of a mandibular model when the model is held by said mandibular model holding device.

17. The assembly tool of claim 14, wherein said vertical support and adjustment means further comprises a means for pivoting said clamp assembly as a whole relative to said mandibular model holding means.

18. The assembly tool of claim 17, wherein said means for pivoting is for pivoting said clamp assembly as a whole in a vertical plane.

19. The assembly tool of claim 18, wherein said means for pivoting comprises a ball and socket joint.

20. An appliance assembly tool, comprising:

a base having a vertical support arrangement thereon;

a mandibular model holding device connected with said base for holding a mandibular model;

a clamp assembly vertically movably mounted on said base above said holding device, said clamp assembly being mounted on said base by said vertical support arrangement, and said clamp assembly comprising first and second clamp supports adjustably mounted with respect to said vertical support arrangement and at least one clamp adjustably mounted on each said clamp;

wherein said clamp assembly is pivotable relative to said mandibular model holding device so as to be capable of positioning said clamps at different angles.

21. The assembly tool of claim 20, wherein said vertical support arrangement comprises an adjustable pivot connection that pivotably connects said clamp assembly relative to said base and said mandibular model holding device such that said clamp assembly is pivotable relative to said mandibular model holding device.

22. The assembly tool of claim 21, wherein said adjustable pivot connection comprises a ball and socket joint.

* * * * *